United States Patent [19]

Lanier et al.

[11] Patent Number: 4,607,007

[45] Date of Patent: Aug. 19, 1986

[54] DIFFERENTIATION OF NATURAL KILLER CELL SUBPOPULATIONS OF CELLS

[75] Inventors: Lewis Lanier, Menlo Park; Noel L. Warner, Los Gatos, both of Calif.

[73] Assignee: Becton, Dickinson and Company, Paramus, N.J.

[21] Appl. No.: 482,752

[22] Filed: Apr. 7, 1983

[51] Int. Cl.[4] .................. G01N 33/53; G01N 33/554; C12Q 1/02; A61K 39/00

[52] U.S. Cl. .......................................... 435/7; 424/85; 435/29; 436/519; 436/537; 436/548; 436/800; 935/110

[58] Field of Search ............... 436/519, 537, 548, 800; 485/2, 7, 29, 948; 424/85, 101; 935/110

[56] References Cited

U.S. PATENT DOCUMENTS 4,284,412  8/1981  Hansen et al. .................... 436/548

OTHER PUBLICATIONS

Titus et al (1982) Texas Red, A Hydrophilic, Red-Emitting Fluorophore for Use with Fluorescein in Dual Paramenter Flow Microfluorometric and Fluorescence Microscope Studies J. of Immunol. Methods 50: 193-204.

Segal et al (1981) Fc(IgG) Receptors on Rat Basophilic Leukemia Cells, J of Immunol. 126(1): 138-145.

Beverley (1982) The Use of Fluorescence Activated Cell Sorter for the Identification and Analysis of Function of Cell Subpopulations, in: Monoclonal Antibodies in Clinical Medicine Ed McMichael & Fabre, pp. 557-584.

*Primary Examiner*—Robert J. Warden
*Assistant Examiner*—Cynthia Lee Foulke
*Attorney, Agent, or Firm*—James R. McBride

[57] ABSTRACT

A method for distinguishing multiple subpopulations of a cell sample whereby human natural killer cells subpopulations can be monitored. The method utilizes two monoclonal antibodies identified as anti-Leu-7 and anti-Leu-11.

12 Claims, 2 Drawing Figures

DIFFERENTIATION OF NATURAL KILLER CELL SUBPOPULATIONS OF CELLS

BACKGROUND OF THE INVENTION

1. Field of the Invention

The present invention relates generally to a method for distinguishing multiple subpopulations of cells, and more particularly, relates to a method for distinguishing and enumerating multiple subpopulations of cells in a manner whereby natural killer cell subpopulations can be monitored.

2. Description of the Prior Art

Considerable attention has recently been given to the study of cells from unimmunized hosts which are capable of lysing tumor cells in vitro. Such cells are commonly referred to as natural killer cells. Natural killer cells may play an important role in malignancy and disease. It is known that the use of certain cancer treatment agents, such as interferon, influences the number and potency of natural killer cells in human blood. Human natural killer cells are known to express a variety of antigens, some of which are common to the T lineage and others to the myeloid lineage. As yet, the differentiation pathway and cellular lineage of these cells are unresolved and this is further complicated by possible heterogeneity in natural killer cells and natural cytotoxicity systems.

It would be desirable to provide a method whereby natural killer cells can be distinguished and enumerated separately from other mononuclear cells, primarily lymphocytes, to permit monitoring changes which may occur in these natural killer cell populations during the development and treatment of disease processes.

SUMMARY OF THE INVENTION

In accordance with the present invention, a method is provided for monitoring natural killer cell subpopulations of human cells. The method includes the steps of providing a sample of cells, usually from the peripheral blood of a human, subjecting the sample to treatment to provide a lymphocyte fraction which contains substantially all of the mononuclear cells including the lymphocyte cells and the natural killer cells. Selected cells of the lymphocyte fraction are then labelled with a first monoclonal antibody conjugated with a first fluorochrome label. Other selected cells of the lymphocyte fraction are labelled with a second monoclonal antibody conjugated with a second fluorochrome label. The labelled cells are then separated into multiple subpopulations by a suitable method such as by examination with a fluorescence microscope or through use of flow cytometry techniques. A preferred method for separating the labelled cells into subpopulations is through use of flow cytometry wherein the lymphocyte fraction containing the labelled cells is passed, substantially one at a time, through an area of focused optical stimulation to provide excitation energy to excite the first fluorochrome label and the second fluorochrome label. The fluorescence emitted by the excited fluorochrome is detected and subpopulations of the lymphocyte cells are distinguished relative to the detected fluorescence characteristics of the first fluorochrome and the second fluorochrome. Through suitable selection of the first monoclonal antibody and the second monoclonal antibody, the relative proportion of natural killer cells in the lymphocyte fraction can be monitored.

DEFINITIONS

Monoclonal Antibodies

A homogeneous antibody obtained from a continuous cell line which is usually produced by the fusion of mouse myeloma cells to spleen cells, first described by Kohler and Milstein (*Nature* 256, 495–497, 1975). The specificity of a particular monoclonal antibody is influenced principally by the type of antigen employed to immunize the host and the selection technique used for isolating the desired cell which is subsequently fused to the myeloma cell to produce the hybrid cell (called "hybridomas"). It is now recognized that a particular monoclonal antibody can be recreated to provide a substantial functional equivalent for any other monoclonal antibody by repetition of the immunization process with the same or related antigens.

FACS TM Cell Sorter

A fluorescence activated cell sorter, manufactured by Becton Dickinson FACS Systems, which is useful for detecting particles such as cells and the like. FACS apparatus commonly includes several detectors for the detection of subpopulations of cells in a mixture. For example, devices are known which include two fluorescent agents associated with the respective fluorescence detectors. In these devices, a fluorescence detector is used for each category of fluorochrome-treated cells to be detected in the mixture of cells in the sample being analyzed. In some cases, a separate light source is used to excite each different type of fluorochrome which has been bound onto a cell to be studied. Apparatus utilizing two light sources for analyzing an equivalent number of fluorochrome tagged particles are described in, for example, U.S. Pat. No. 3,826,364 and U.S. Pat. No. 4,284,412. Additional instrumentation utilized mercury arc lamp sources for light excitation, such as in the FACS TM Analyzer, manufactured by Becton Dickinson FACS Systems.

Anti-Leu-7

A designation for commercially available monoclonal antibody which recognizes a subset of peripheral blood lymphocytes. The subset recognized is from about 10% to 25% of the total population of peripheral blood lymphocytes and includes some but not all of the human natural killer cell population. Anti-Leu-7 is characterized in that it will react with HSB-2 tumor cell line, recognizes 10% to 25% of peripheral blood lymphocytes and has a characteristic FACS TM Cell Sorter profile. A monoclonal antibody which is equivalent to anti-Leu-7 can be recognized by reacting the suspected equivalent monoclonal antibody with HSB-2 tumor cell line and subsequently reacting the treated HSB-2 tumor cell line with commercially available anti-Leu-7. If the commercially available anti-Leu-7 does not react with the HSB-2 tumor cell line reacted with the suspected equivalent monoclonal antibody, such monoclonal antibody is the substantial functional equivalent of anti-Leu-7.

Anti-Leu-11

A commercially available monoclonal antibody produced by immunization with large granular lymphocytes. Anti-Leu-11 is available in two forms, anti-Leu-11*a* and anti-Leu-11*b*, both forms are useful in the present invention and are referred to herein collectively as anti-Leu-11. Anti-Leu-11*a* was produced by immunization with large granular lymphocytes purified by percoll gradients (Pharmacia Fine Chemicals, Piscataway, N.J. Anti-Leu-11*b* was produced by immunization against granulocytes. Anti-Leu-11 reacts with substantially all of the neutrophil components of granulocytes, i.e. at least about 90%. Anti-Leu-11 reacts with from about 10% to 20% of the peripheral blood lymphocytes and essentially all natural killer cells in peripheral blood. Anti-Leu-11 does not react with the eosinophil component of granulocytes. Anti-Leu-11 has strong Fab binding to the Fc receptor sites on granulocytes. Non-anti-Leu-11 monoclonal antibodies have the usual random Fc binding properties of monoclonal antibodies to Fc receptors on granulocytes. A monoclonal antibody which is functionally equivalent to anti-Leu-11, when reacted with granulocytes, will prevent any further substantial binding of IgG aggregates. IgG aggregates can be produced by binding fluorescein isothiocyanate (FITC) to rabbit IgG and subjecting the labelled rabbit IgG to a temperature of 65° C. for one-half hour. A monoclonal antibody which equivalent to anti-Leu-11 can be recognized by reacting the suspected equivalent monoclonal antibody with large granular lymphocytes and subsequently reacting the treated large granular lymphocytes with commercially available anti-Leu-11. If the commercially available anti-Leu-11 does not react with the large granular lymphocytes, treated with the suspected equivalent monoclonal antibody, such monoclonal antibody is substantial functional equivalent of anti-Leu-11.

Lymphocyte fraction refers to a suspension of cells which include substantially all of the mononuclear cells including the natural killer cells from a sample of cells, usually a blood sample, taken from a human subject.

Figure 1:
FIG. 1 is a graphic representation of multiple subpopulations of lymphocyte cells produced in accordance with the present invention.
Figure 1:
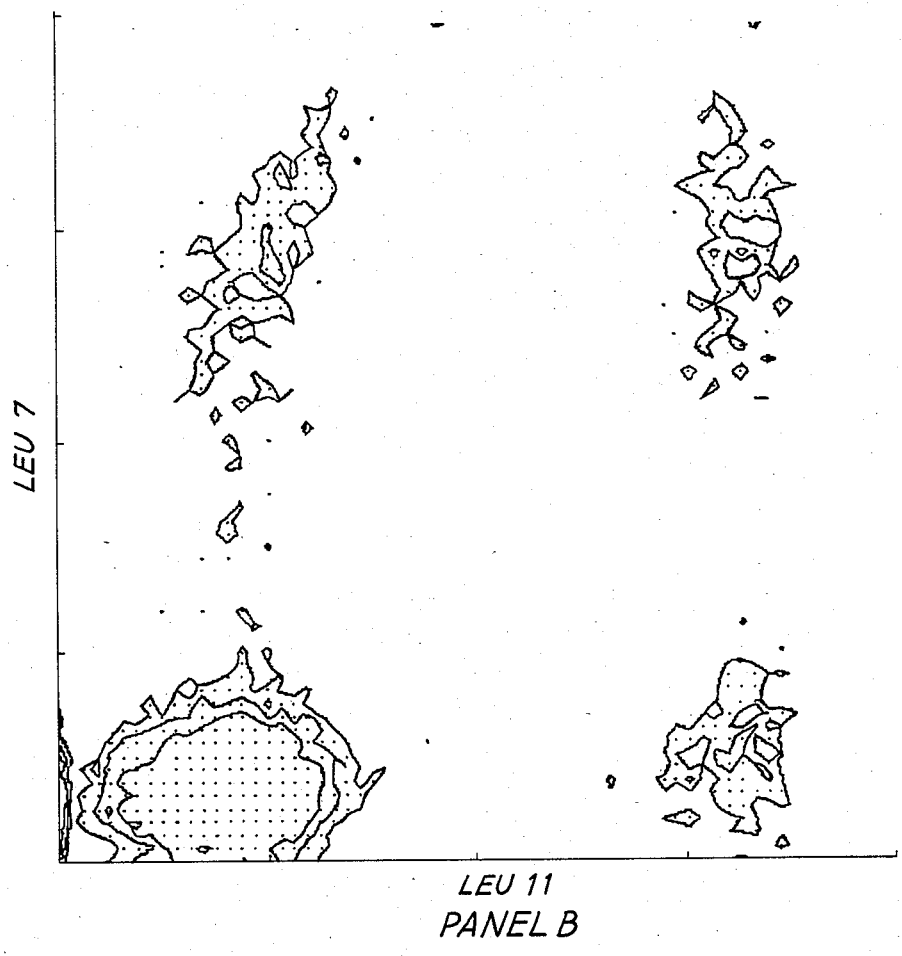

In accordance with the invention, a sample of human cells, usually peripheral blood, is subjected to treatment to provide a lymphocyte fraction which contains substantially all of the mononuclear cells including the natural killer cells. The mononuclear cells are isolated from the patient's blood by a suitable method, such as the Ficoll-Hypaque density gradient method described in T. ABO, et al "A differentiation antigen of human NK and K cells identified by a mononuclear antibody" (HNK-1), J. Immunol. 127:1024 (1981). It should be understood that the cell sample may be derived from sources other than blood. For example, ascites fluid or tissue sections may be used to provide a cell population containing natural killer cells which can be monitored by the method of the invention.

It should be understood that the identification of the total lymphocyte fraction need not utilize Ficoll-Hypaque or similar separation. Total lymphocyte fraction, for example, could be provided on the basis of other biophysical properties of such cells including volume and light scatter, and then detecting such cells in an unseparated blood sample using appropriate instrumentation such as a FACS TM Cell Sorter or FACS TM Analyzer.

In one embodiment of the invention, anti-Leu-11 is fluoresceinated with FITC and added to the lymphocyte fraction. Anti-Leu-7 monoclonal antibody is biotinylated and added to the lymphocyte fraction. A second fluorochrome, such as Texas Red conjugated to avidin or phycoerythrin-B conjugated avidin, is then added to the lymphocyte fraction. The fluorochrome labelled avidin binds to the biotinylated monoclonal antibody by the well known biotin-avidin coupling reaction.

Anti-Leu-7 and anti-Leu-11 are then labelled with a first fluorochrome and a second fluorochrome respectively. The first and second fluorochromes are selected so as to have a detectable emission difference, preferably at least about 25 nm. The fluorochrome may be conjugated to the monoclonal antibody prior to addition of the monoclonal antibody to the lymphocyte fraction. Alternatively, the biotin-avidin coupling reaction may be used to conjugate the fluorochrome to the monoclonal antibody in situ, after the monoclonal antibody is added to the lymphocyte fraction.

It should be understood that various pairings of fluorochromes can be used as the first and second fluorochrome. In general, it is only necessary that the first and second fluorochrome have detectable emission difference. Other potential pairs of fluorochromes include one of the monoclonal antibodies conjugated to fluorescein or rhodamine and the other monoclonal antibody conjugated to phycoerythrin or Texas Red. In addition, other phycobiliprotein compounds could be used in different combinations as the first and second fluorochromes. Fluorescence excitation of fluorescein can be achieved using the 488 nm line of an argon laser, Texas Red can be excited using the 568 nm line of krypton laser or by using rhodamine 6G dye lasers with excitation around 600 nm.

The labelled cells are then passed, substantially one at a time, through a FACS TM Cell Sorter to provide excitation energy to excite the first and second fluorochrome. A typical printout of a lymphocyte fraction treated and labelled as described hereinabove is set forth in FIG. 1. As shown in FIG. 1, the four subpopulations of cells are described as Leu 7+, Leu 11−; Leu 7+, Leu 11+; Leu 7−, Leu 11−; and Leu 7−, Leu 11+ in accordance with their relative position in respect to the Leu 7 Y-axis and the Leu 11 X-axis. The Leu 7−, Leu 11+, subpopulation has a high natural killer function and comprises approximately a small percentage (usually <10%) of normal peripheral blood lymphocytes. The Leu 7+, Leu 11+ subpopulation has some natural killer function while the Leu 7−, Leu 11− subpopulation has no natural killer function. The Leu 7+, Leu 11− subpopulation has some natural killer function.

By examining the peripheral blood of a patient on a periodic basis, while the patient is undergoing treatment, the natural killer subpopulations can be monitored to provide information concerning the effectiveness of the treatment. In addition the method can be used for diagnostic screening to provide information concerning the immune status of an individual.

The following example further illustrates various features of the invention but is not intended to limit the scope of the invention as set forth.

EXAMPLE

Human peripheral blood was collected into sodium heparin coated 15 ml tubes. The blood was diluted 1:1 in phosphate buffered saline (0.1 M phosphate, ph 7.3). Fifteen ml of Ficoll-Paque (Pharmacia Fine Chemicals, Piscataway, N.J.) was added to a 50 ml conical centrifuge tube and the blood was gently layered onto the Ficoll-Paque. This was centrifuged at 570×g for 45 min. at room temperature in a swinging bucket rotor. After centrifugation, the lymphocyte fraction containing the mononuclear cells was removed from the interface of the gradient. These cells were washed twice in 50 ml phosphate buffered saline and were adjusted to a concentration of $2 \times 10^7$/ml in phosphate buffered saline containing 0.1% sodium azide.

Anti-Leu-7 and anti-Leu-11 monoclonal antibodies, obtained from Becton Dickinson Monoclonal Center, Inc., Mountain View, Calif. were used for this example. Anti-Leu-11a and anti-Leu-11b monoclonal antibodies were secreted by the NKP-15 and G022 hybridoma cell lines, respectively. Anti-Leu-7 monoclonal antibody was secreted by the HNK-1 hybridoma cell line. All antibodies were purified by routine and standard antibody purification techniques. Fluorescein isothiocynate (FITC) was conjugated to the antibodies by the widely used method described by Goding (1). Antibodies were conjugated to biotin by standard methods, such as the procedure described by Goding (2). Texas Red dye was conjugated to avidin by the method described by Hayakawa et al. (3). Phycoerythrin-B was conjugated to avidin essentially by the method described by Oi et al. (4).

TWO COLOR IMMUNOFLUORESCENCE STAINING

One million mononuclear leukocytes in a total volume of 50 microliters diluent were placed into 12×75 mm polystyrene tubes. One microgram of fluorescein (FITC) conjugated anti-Leu-11a antibody in 10 microliters diluent was added to each tube. The tubes were vortexed, and after 15 min., 3 ml diluent were added to each tube and the samples were centrifuged at 400×g for 5 min. The supernatant was removed and one microgram of biotin conjugated anti-Leu-7 antibody in a total volume of 10 microliters diluent were added to each tube. The samples were vortexed and incubated for an additional 15 min. Three ml diluent was added and the samples were centrifuged at 400×g for 5 min. The supernatant was removed and 0.5 micrograms Texas Red (TR) avidin or 1.0 micrograms phycoerythrin (PE) avidin in 50 microliters diluent was added to each tube. After an additional 15 min. incubation the cells were washed twice in 1 ml diluent, the supernatant was removed and the cell pellet was resuspended in a 1% paraformaldehyde/0.85% saline solution. The fixed cells were stored at 4° C. in the dark until analysis. All dilutions and cell washing were performed in cold phosphate buffered saline (0.1 M phosphate, pH 7.2) contained 0.1% sodium azide and all procedures were carried out at 4° C.

Dead cells, erythrocytes, granulocytes, monocytes and platelets were excluded from analysis by setting an appropriate threshold trigger on the low forward angle and 90 degree light scatter parameters. Low angle forward light scatter, 90 degree light scatter, green fluorescence, and red fluorescence were stored in list mode using a Consort 40 PDP/11 based computer system (Becton Dickinson FACS Division, Sunnyvale, Calif.). Single parameter data were displayed as histograms with fluorescence channel on the x-axis and relative number of cells on the y-axis. In determining the % positive cells, a marker was set on the appropriate control histogram such that 5% or less of the cells were to the right of this channel marker. Using this as a reference point, the % cells in the specific antibody stained sample histogram was calculated, and the control % was subtracted from this value.

Essentially identical procedures for gating and analysis were used with the FACS TM analyzer with Consort 20 or 30 Computer Systems except that light excitation was provided by mercury arc lamp, and volume and 90° light scatter were used for gating.

Two parameter data were collected into a 64×64 matrix and displayed as contour maps. "Contours" were drawn to indicate increasing numbers of cells in a defined area of the array as described hereinbelow in a discussion of FIGS. 1 and 2.

FIG. 1. Human peripheral mononuclear cells from two individuals were isolated from Ficoll Hypaque gradient and were stained as follows: Panel A–FITC anti-Leu-11a and biotin anti-Leu-7/Texas Red avidin, or Panel B FITC anti-Leu-11a and biotin anti-Leu-7/Phycoerythrin avidin. Cells were anlyzed using a FACS TM Cell Sorter apparatus calibrated for appropriate excitation and emission detection for the fluorochrome systems. The lymphocyte component of the mononuclear cells was discriminated by their characteristic low forward angle and 90° light scatter. The green fluorescence and red fluorescence (for Texas Red) or orange-red fluorescence (for Phycoerythrin) were displayed in 2 dimensional contour maps. X axis=green fluorescence (i.e. FITC anti-Leu-11a); y axis=red fluorescence (i.e. TR avidin/biotin anti-Leu-7) or red-orange fluorescence (i.e. Phycoerythrin avidin/biotin anti-Leu-7). In Panel A, concentric contours were drawn to enclose areas which contained more than 10, 20 and 30 cells. In Panel B, contours were drawn to enclose areas with more than 5, 10 and 20 cells. Note that in both examples, four discrete populations of cells are evident. (e.g. Leu 11a+, 7+, Leu 11a+, 7−, Leu 11a, 7+, and Leu 11a−, 7−). Each of the subpopulations was examined for natural killer cell activity by the method described by Warner et al (5). The amount of natural killer cell activity found in each of the four subpopulations was substantially different.

Figure 2:
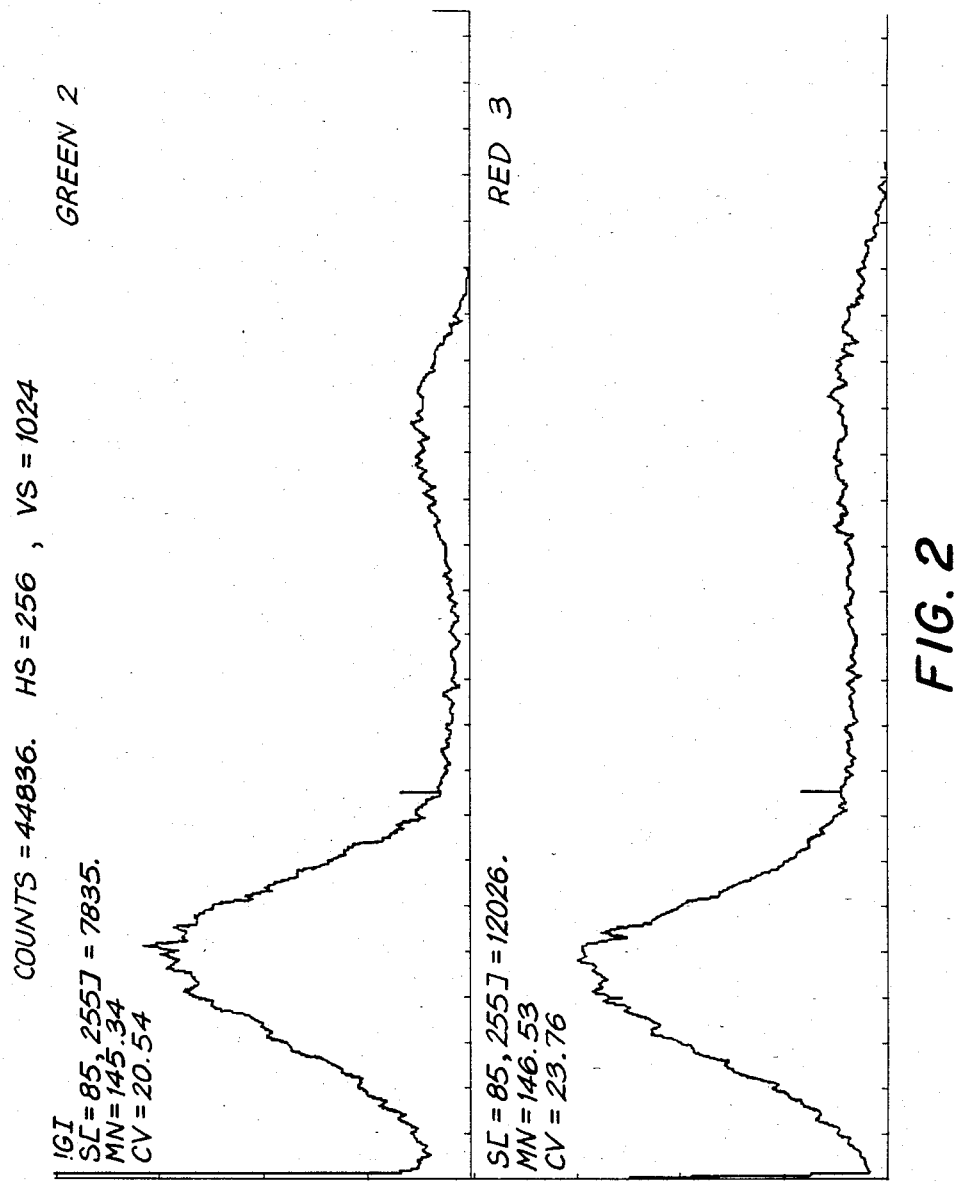
FIG. 2 is a FACS TM Cell Sorter histogram profile of anti-Leu-11 labelled with fluorescein and anti-Leu-7 labelled with phycoerythrin.

FIG. 2. The green fluorescence (e.g. top panel, FITC anti-Leu-11a) and red fluorescence (e.g. bottom panel Texas Red avidin/biotin-anti-Leu-7) histograms of the lymphocytes described in FIG. 1 Panel A are demonstrated. The X axis represents 256 fluorescence channels, with increasing fluorescence intensity from left to right. The Y axis represents number of cells in each channel.

In the top panel, cells in channels 85–255 would be considered "positive" for the Leu 11a antigen (about 17.5% of lymphocytes). In Panel B, cells in channels 85–255 would be considered "positive" for the Leu 7 antigen (about 26.8% of lymphocytes).

References:
1. Goding, J. W. 1976. Conjugation of antibodies with fluorochromes: modifications to the standard methods. J. Immunol. Meth. 13:215.
2. Goding, J. W. 1980. Antibody production by hybridomas. J. Immunol. Meth. 39:285.
3. Hayakawa, K., R. R. Hardy, D. R. Parks, and L. A. Herzenberg, 1983. The "Lyl B" cell subpopulation in normal, immunodefective, and autoimmune mice, J. Exp. Med. 157:202.
4. Oi, V. T., A. N. Glaser, and L. Stryer, 1982, Fluorescent phycobiliprotein conjugates for analyses of cells and molecules. J. Cell Biology 93:981.

5. Warner et al, 1981, Analysis of the Differentiation Lineage of N. K. Cells, Federation Proceedings, Vol. 40, Pg. 2711.

What is claimed is:

1. A method for monitoring natural killer cell subpopulations in human blood comprising
    (a) providing a sample of cells containing a population of natural killer cells;
    (b) labelling selected cells of said sample with anti-Leu-11 monoclonal antibody coupled with a first fluorochrome label;
    (c) labelling selected cells of said sample with anti-Leu-7 monoclonal antibody coupled with a second fluorochrome label, said first fluorochrome label and said second fluorochrome label having a detectable emission difference;
    (d) providing excitation energy to excite said first fluorochrome label and said second fluorochrome label;
    (e) detecting the fluorescence emitted by the excited fluorochromes; and
    (f) distinguishing subpopulations of cells relative to the detected fluorescence characteristics thereof, whereby the relative proportion of natural killer cells in said subpopulations can be monitored.

2. A method in accordance with claim 1 wherein said sample of cells is a peripheral blood sample.

3. A method in accordance with claim 2 wherein said blood sample is treated to provide a lymphocyte fraction comprising substantially all of the mononuclear cells including natural killer cells prior to the step of labelling said selected cells.

4. A method in accordance with claim 3 wherein said first fluorochrome label is selected from the group consisting of fluoroscein, rhodamine and a phycobiliprotein and said second fluorochrome label is selected from the group consisting of Texas Red and a phycobiliprotein.

5. A method in accordance with claim 3 wherein said first fluorochrome is fluorescein and said second fluorochrome is Texas Red.

6. A method in accordance with claim 3 wherein said first fluorochrome is fluorescein and said second fluorochrome is phycoerythrin.

7. A method in accordance with claim 1 wherein said labelled cells are passed, substantially one at a time, through an area of focused optical stimulation to provide excitation energy to excite said first fluorochrome label and said second fluorochrome label.

8. A method in accordance with claim 1 wherein said first fluorochrome label is selected from the group consisting of fluorescein, rhodamine and a phycobiliprotein and said second fluorochrome label is selected from the group consisting Texas Red and a phycobiliprotein.

9. A method in accordance with claim 1 wherein said first fluorochrome is fluorescein and said second fluorochrome is Texas Red.

10. A method in accordance with claim 1 wherein said first fluorochrome is fluorescein and said second fluorochrome is phycoerythrin.

11. A method in accordance with claim 1 wherein said fluorescence detection is accomplished by means of a fluorescence microscope.

12. A method in accordance with claim 1 wherein said fluorescence activated cell sorter.

* * * * *